(12) United States Patent
Shavelson

(10) Patent No.: US 12,090,117 B2
(45) Date of Patent: Sep. 17, 2024

(54) METHOD OF ADMINISTERING NANOPARTICLES THROUGH FEET

(71) Applicant: Dennis Shavelson, Tampa, FL (US)

(72) Inventor: Dennis Shavelson, Tampa, FL (US)

( * ) Notice: Subject to any disclaimer, the term of this patent is extended or adjusted under 35 U.S.C. 154(b) by 666 days.

(21) Appl. No.: 17/444,961

(22) Filed: Aug. 12, 2021

(65) Prior Publication Data

US 2022/0047456 A1 Feb. 17, 2022

Related U.S. Application Data

(60) Provisional application No. 63/038,192, filed on Jun. 12, 2020.

(51) Int. Cl.
  *A61H 35/00* (2006.01)
  *A61H 23/00* (2006.01)
  *B82Y 5/00* (2011.01)

(52) U.S. Cl.
  CPC ........... *A61H 35/006* (2013.01); *A61H 23/00* (2013.01); *A61H 2201/0207* (2013.01); *A61H 2201/14* (2013.01); *A61H 2201/165* (2013.01); *B82Y 5/00* (2013.01)

(58) Field of Classification Search
  CPC .................................................... A61H 35/006
  See application file for complete search history.

(56) References Cited

U.S. PATENT DOCUMENTS

| | | | |
|---|---|---|---|
| 1,754,971 A * | 4/1930 | Waigand | A61H 35/00 604/23 |
| 2,904,037 A | 9/1959 | Cassidy | |
| 3,055,357 A | 9/1962 | Redka | |
| 3,478,738 A * | 11/1969 | Cox | A61H 35/006 36/2.6 |
| 4,513,735 A | 4/1985 | Friedson et al. | |
| 4,620,529 A | 11/1986 | Kurosawa | |
| 5,688,225 A * | 11/1997 | Walker | A61H 9/005 601/151 |
| 6,805,678 B2 | 10/2004 | Cafaro | |
| 7,065,808 B2 | 6/2006 | Leung et al. | |
| 8,407,822 B2 | 4/2013 | Park | |
| 9,308,388 B2 | 4/2016 | Chau | |
| 10,813,831 B2 * | 10/2020 | Hemmrich | A61P 9/14 |
| 11,478,656 B2 * | 10/2022 | Giles | A61M 21/0094 |
| 11,596,275 B2 * | 3/2023 | Sedic | A61H 23/0263 |
| 2002/0056158 A1 | 5/2002 | Ferber et al. | |

(Continued)

*Primary Examiner* — LaToya M Louis
(74) *Attorney, Agent, or Firm* — Dunlap Bennett & Ludwig, PLLC; Anna L. Kinney

(57) ABSTRACT

A therapeutic nanoparticle diffusion system includes at least one rubber bootie; a foot bath; and a nanoparticle composition. The rubber bootie is adapted to accommodate a user's foot and the nanoparticle composition. The foot bath has a predetermined height, a vibrational base, and a heating element attached. A therapeutic method of administering nanoparticles includes providing the bootie and the foot bath; adding water to the foot bath; donning the bootie; resting the foot and the bootie in the foot bath; adding a nanoparticle composition to the bootie; activating the heating element and the vibration element; resting the subject's foot in the nanoparticle composition; doffing and emptying the bootie into the foot bath; and soaking the subject's foot in the foot bath. The temperatures and times are predetermined.

12 Claims, 4 Drawing Sheets

(56) References Cited

U.S. PATENT DOCUMENTS

| | | | | |
|---|---|---|---|---|
| 2005/0066547 | A1* | 3/2005 | Al-Rasheed | A43B 7/1455 |
| | | | | 36/95 |
| 2005/0277854 | A1* | 12/2005 | Hatchett | A61H 35/006 |
| | | | | 601/158 |
| 2006/0207018 | A1* | 9/2006 | Lev | A61H 33/02 |
| | | | | 4/622 |
| 2008/0038375 | A1* | 2/2008 | Park | A61H 35/006 |
| | | | | 424/715 |
| 2010/0324611 | A1* | 12/2010 | Deming | A43B 7/147 |
| | | | | 607/2 |
| 2014/0250583 | A1 | 9/2014 | Sergi et al. | |
| 2017/0361123 | A1* | 12/2017 | Efremkin | A61N 5/0624 |
| 2022/0266046 | A1* | 8/2022 | Giles | A61F 7/0053 |

* cited by examiner

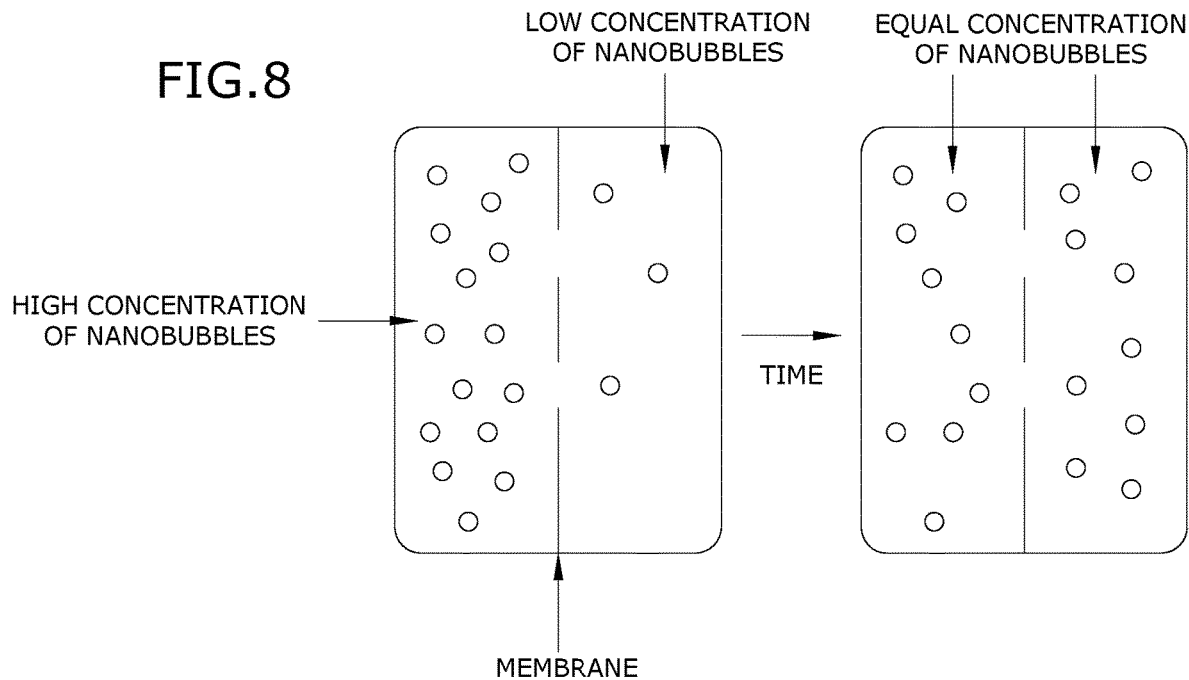
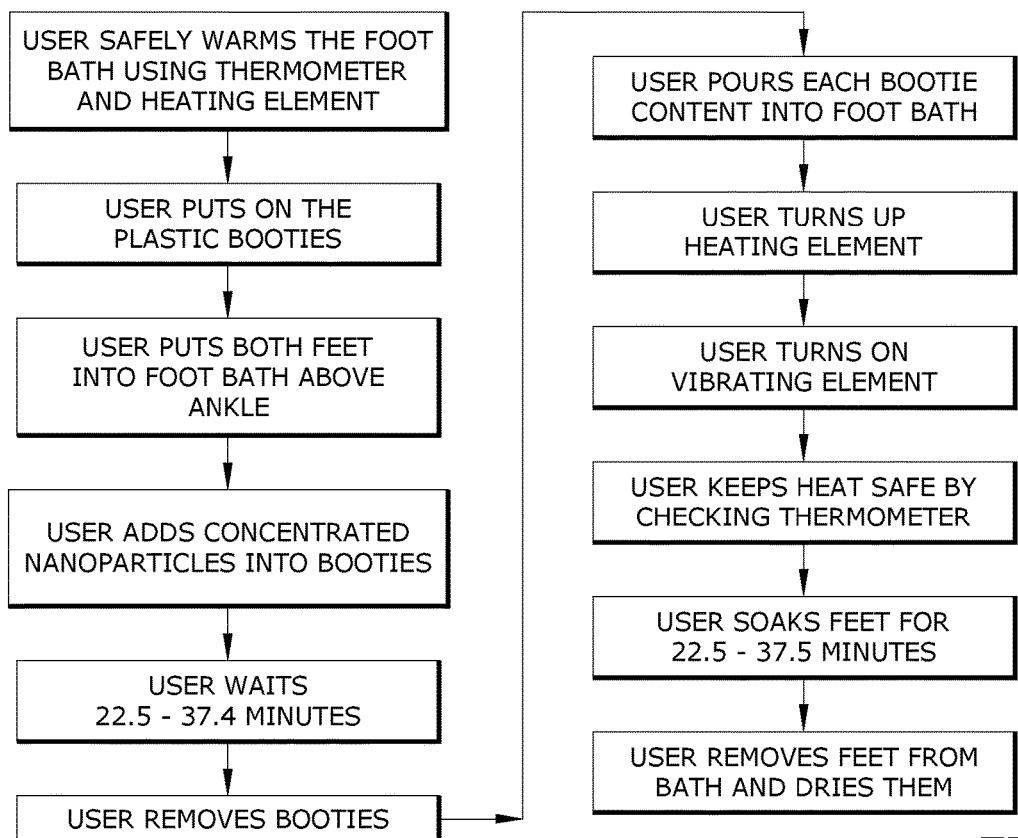

METHOD OF ADMINISTERING NANOPARTICLES THROUGH FEET

CROSS-REFERENCE TO RELATED APPLICATION

This application claims the benefit of priority of U.S. provisional application No. 63/038,192, filed Jun. 12, 2020, the contents of which are herein incorporated by reference.

BACKGROUND OF THE INVENTION

The present invention relates to transmitting therapeutics through membranes and, more particularly, to a method of administering nanoparticles through feet.

There has long been interest in administering pharmaceutical agents through the skin without the pain and anxiety associated with a needle puncture.

Nanoparticles (<100 nm) have been considered a promising new class of therapeutics, in part because they may be transmitted through cell membranes when other compositions do not. Nanoparticles are injected, painted, applied topically orally or sublingual but have rarely been diffused in a solvent. Currently available uses of nanoparticles require large amounts of nanoparticles, are expensive, and have limited applications.

Currently available therapeutic methods to push particles across the skin, tissues, and cell membranes (referred to herein as phoresis) utilize electric currents, sound waves or magnetic fields that have side effects and may not be safe. Existing methods of electrophoresis, magnetophoresis and phonophoresis require the addition of potentially harmful energy forces to bombard the body. They have poor and weak outcomes therapeutically, i.e., they are ineffective. Moreover, existing phoresis therapies are not targeted to the feet.

As can be seen, there is a need for a means of driving active ingredients through skin or a cell membrane without electricity, magnetism, or sound waves and in high enough concentrations to be therapeutic

SUMMARY OF THE INVENTION

In one aspect of the present invention, a therapeutic nanoparticle diffusion system is provided, comprising: at least one rubber bootie adapted to accommodate a user's foot and a nanoparticle composition; a foot bath with a predetermined height and having a vibrational base and a heating element coupled to the foot bath; and the nanoparticle composition.

In another aspect of the present invention, a therapeutic method of administering nanoparticles is provided, comprising: providing at least one bootie and a foot bath with a heating element and a vibration element; adding water at a first temperature to the foot bath; donning the at least one bootie on a subject's foot; resting the subject's foot and the at least one bootie in the water in the foot bath for a first predetermined time; adding a nanoparticle composition to the at least one bootie; activating the heating element to maintain a second temperature and the vibration element; resting the subject's foot in the nanoparticle composition for a second predetermined time; doffing the at least one bootie and emptying the at least one bootie into the foot bath and adjusting the foot bath to maintain a third temperature; and soaking the subject's foot in the foot bath for a third predetermined time.

These and other features, aspects and advantages of the present invention will become better understood with reference to the following drawings, description, and claims.

BRIEF DESCRIPTION OF THE DRAWINGS

FIG. 8 is an illustration of the nanophoresis; and

FIG. 9 is a flow chart of the nanophoresis methodology.

DETAILED DESCRIPTION OF THE INVENTION

Figure 1:
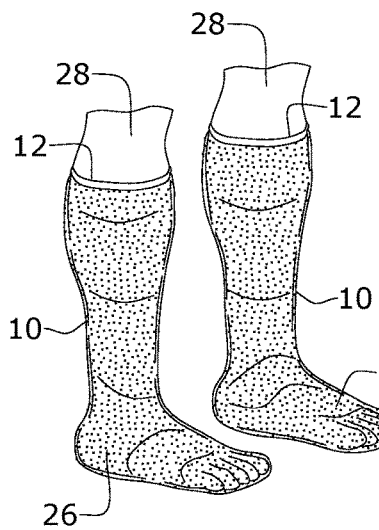
FIG. 1 is a perspective view of booties used in a first step of a therapeutic method according to an embodiment of the present invention, shown in-use.

The following detailed description is of the best currently contemplated modes of carrying out exemplary embodiments of the invention. The description is not to be taken in a limiting sense but is made merely for the purpose of illustrating the general principles of the invention, since the scope of the invention is best defined by the appended claims.

Broadly, one embodiment of the present invention is a method of nanoparticle diffusion therapy.

This methodology utilizes nanoparticles or nanobubbles small enough to pass through the skin and/or tissues and cell membranes and into the circulation by diffusion. It is enhanced biologically by using the materials, anatomical location and methodology presented here without applying additional forces such as magnets, electricity and/or sound waves.

The inventive methodology works by diffusion rather than by osmosis. This invention increases the diffusion process through the skin. It works with less active ingredient, is safer and less expensive, and provides deeper tissue and cellular penetration than previous methodologies. This invention increases the amount of active ingredient that enters the circulation to therapeutic levels. Since the therapeutic agent enters the circulation, the invention has the potential to treat a subject's full body.

The foot is the preferred location for treatment due to its anatomy, the distance of the heart, and the fact that its circulation is gravity dependent and because it is the most vulnerable area to pathology in almost all systems. A foot holds about 1.5% of the total blood volume. Its low volume of blood, the anatomy of the skin to bone depth, and the complexity of the tissues in a small space make the foot the optimal anatomical location for nanoparticle diffusion therapy.

Variations and alterations of the methodology may expand the invention to use in other biological and non-biological arenas. By increasing the amount of solution, using different active ingredients, utilizing vessels of various sizes and materials, different heating and vibratory elements, different encapsulating elements (e.g., the booties), and/or varying the materials used to envelope the intended host element while maintaining a high concentration of useful nanoparticles, the component parts and methodology may be where useful nanoparticles may be diffused through membranes and solid materials that have pores larger than the nanoparticles (>100 nm). Applications in manufacturing, servicing and maintenance, and many other biological, mineral, and metallic and mechanical hosts and uses are contemplated.

The inventive method utilizes a vesicle to hold the feet and water to make a foot bath. A plastic booty and/or foot bath holds less than about 1.5-2.0 gallons of water. In this volume, a small amount of active ingredient develops high enough concentrations to force diffusion to occur through skin and deeper tissues with therapeutic outcomes. The booties in particular enable the concentration of the nanoparticles in solution to be at its highest. The small volume also increases contact of the nanoparticles with the skin of the subject for increased, deeper diffusion through the skin and tissues.

A thermostatic heating element is provided to raise the bath temperature, increasing diffusion of active ingredient from the bath into the feet. The heat element keeps the water temperature warm. Diffusion generally works best at or near, and not above, body temperature (e.g., below about 90° F.).

A mild vibration element is provided to keep the nanoparticles in solution throughout the foot bath and to reduce surfacing or evaporation of the nanoparticles. Mild vibration excites the nanoparticles to have more Brownian Movement which also increases diffusion of the active ingredient.

The bolus comprises a nanoparticle solution or gel with a concentration generally in the billions of nanoparticles. The solvent or emulsion matrix keeps the nanoparticles separated and moving for longer shelf life.

The treatment occurs for preferably more than about 30 minutes up to about one hour 15 minutes to maximize both pedal and full body therapeutic effect. For example, the treatment may be applied for an average of 50 minutes. A timer may be used to ensure each method step falls within a predetermined timeframe. The methodology of the treatment has separate components, each with its own purpose that when combined provides the best therapeutic outcomes. The total effect of the system produces an optimal effect greater than the sum of its parts.

A method according to an embodiment of the present invention may include the following steps.

Step 1: the subject may put one or both feet to be treated into an empty plastic bootie(s). For about 5 minutes, the subject may rest the foot or feet in a cool foot bath filled with water deep enough to submerse the feet above the ankles. The cool temperature is operative to constrict pedal blood vessels, reducing the active ingredient concentration within each foot. This increases the difference between the exogenous-endogenous active ingredient concentration facilitating diffusion of the active ingredient into the foot and deeper into the tissues as active ingredient is added into the booties or the foot bath.

Step 2: a predetermined bolus of active ingredient may be added into the top of the empty bootie (one foot treatment) or booties (two-foot treatment) to cover the ankles and the feet evenly. The heating element may be turned on (at a medium setting or lower) and the mild vibration motor may be turned on. Over the next about 20 minutes, these active nanoparticles may deeply diffuse through the skin and layers of tissue. Shorter than suggested booty bath time reduces the amount of active ingredient diffused and longer than suggested booty bath time does not add enough additional diffusion of active ingredient to be valuable.

Step 3: the subject may remove the booties from one or both feet and place the legs/feet back into the foot bath barefooted. The solution or emulsion containing active ingredient may be poured from the booties directly into the foot bath. Warm water may be added to the foot bath to a level above the ankles to increase the temperature of the bath within the subject's tolerance. The warm water bath enables greater diffusion of the active ingredient across the skin and into the deeper tissues, and is operative to dilate the blood vessels. This causes the nanoparticles to continue to diffuse deeply into the feet. Over the next about 25 minutes (about 22.5-37.5 minutes), the nanoparticles may diffuse through the dilated pedal blood vessels from the Tunica Externa to the Tunica Intima of the blood vessels, into the circulation system. The therapeutic particles are carried by the circulation system throughout the entire body.

After a total of about 50 minutes, the feet may be taken out from the foot bath, rinsed, and dried to remove any active ingredient, ending the treatment. By following the above listed steps, therapeutic biochemical, biological, and medical treatments of nanoparticles may be delivered by infusion into the feet that integratively affect the holistic body.

Adding the active ingredient directly into the foot bath from the booties for Step 3 continues the diffusion of active ingredient through the skin and deeper into the tissues. By this time, the concentration of nanoparticles in the tissues has reached the blood vessels of the circulation (which are more superficial in the foot than in other body locations). During this time, since the concentration of the active ingredient is higher on the outside of the blood vessels than inside the blood vessels, the active ingredient enters the circulation and is carried into the entire body. This diffusion continues when there is patent circulation (no peripheral vascular disease [PVD]) as the blood moves away from the foot, keeping the concentration in the blood lower than the tissues surrounding the blood vessels, thereby continuing the process.

The timing of the different steps and the heat component of the third step of the methodology may be manipulated on a case-by-case basis dependent on the circulation, the neurological status, the size and weight of the subject, the quality of the tissue, and other variables among existing cohorts.

Figure 2:
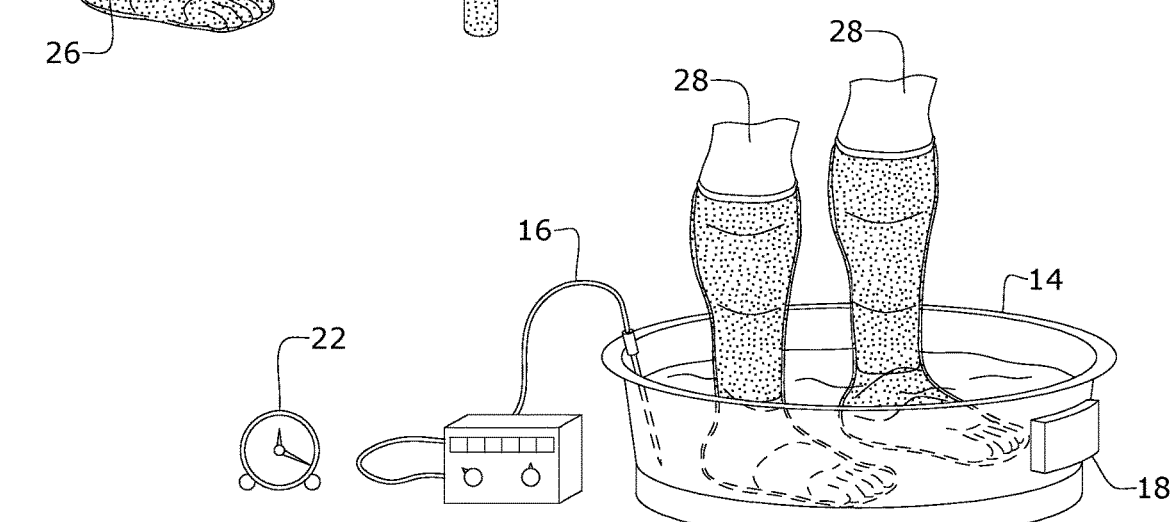
FIG. 2 is a perspective view of a second step of the therapeutic method.
Figure 3:
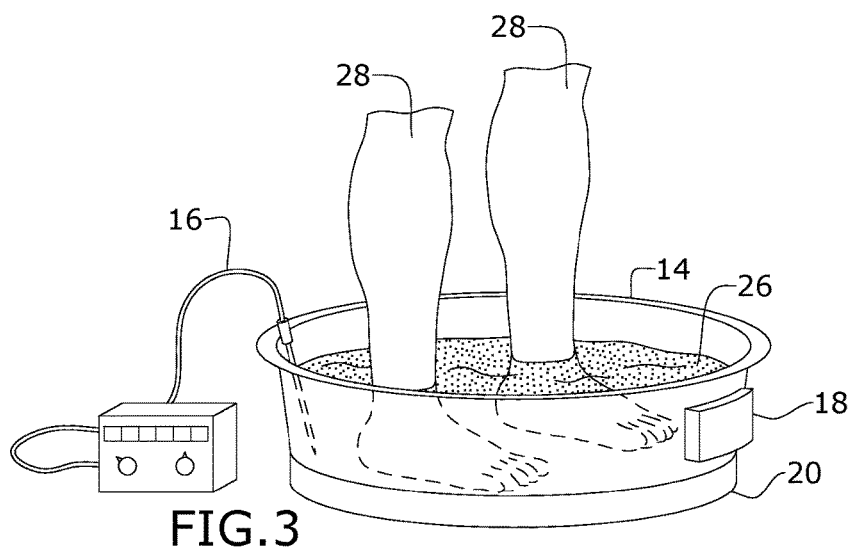
FIG. 3 is a perspective view of a third step of the therapeutic method.

Referring to FIGS. 1 through 8, FIG. 1 illustrates booties 10 comprising an elastic binder 12 holding nanoparticles 26 against a user's legs and feet 28. A source of concentrated nanoparticles 24 is also shown. As shown in FIG. 2, the user may rest the booties 10 and feet 28 in a foot bath 14 comprising a heating element 18 and a vibration motor 20 for a first predetermined period of time, monitored by a timer 22, and at a predetermined temperature, monitored by a thermometer 16. Once the first predetermined period of time has expired, the user may empty the booties 10 into the foot bath 14 and may soak their legs and feet 28 for a second predetermined period of time at a second predetermined temperature.

Figure 4:
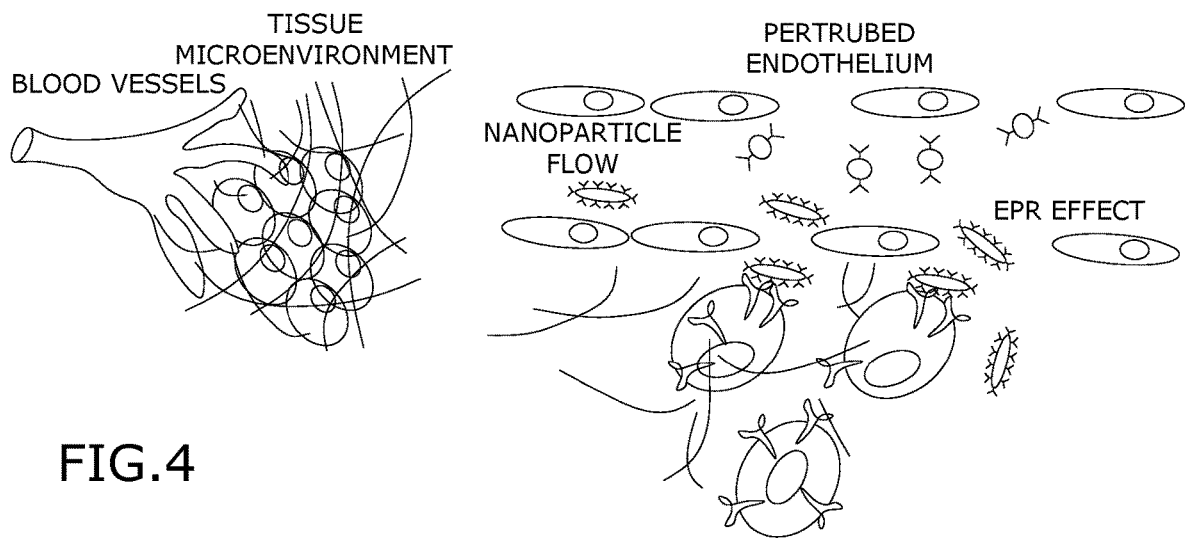
FIG. 4 is an illustration of the endothelial barrier.
Figure 5:
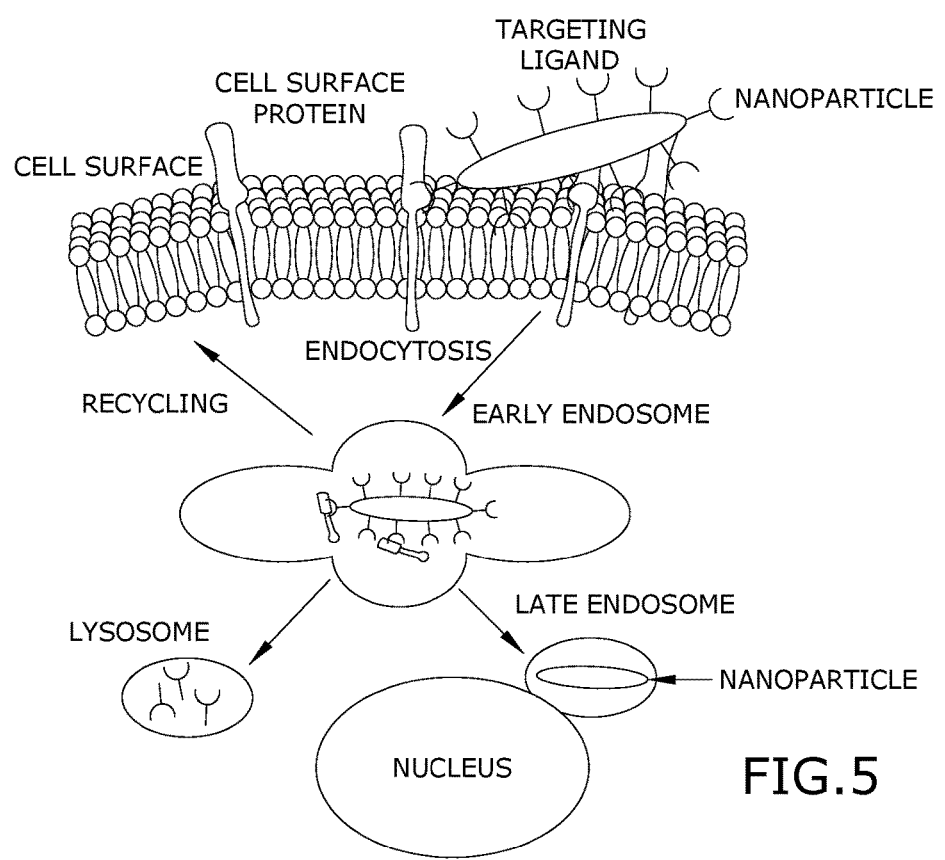
FIG. 5 is an illustration of the cellular barrier.
Figure 6:
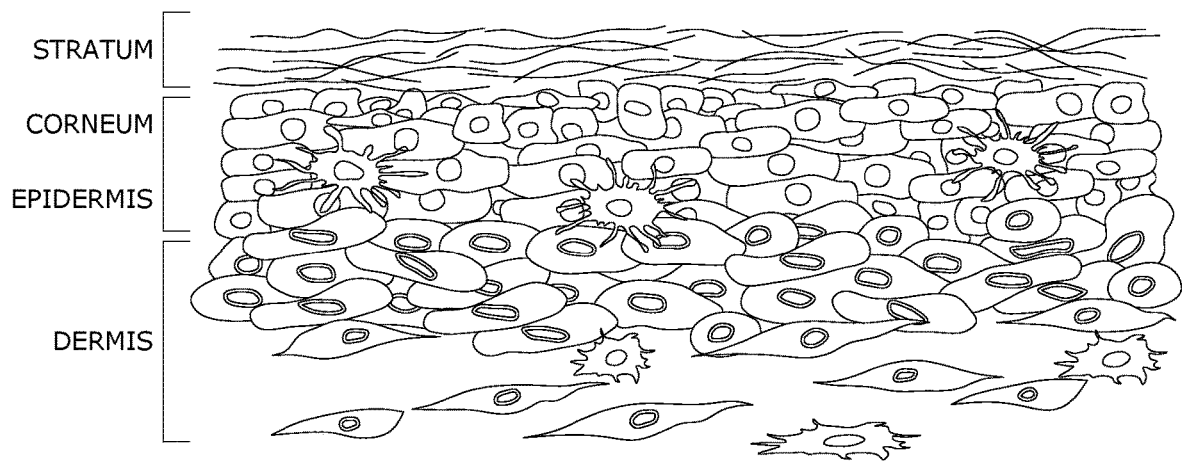
FIG. 6 is an illustration of the skin and mucosal barrier.
Figure 7:
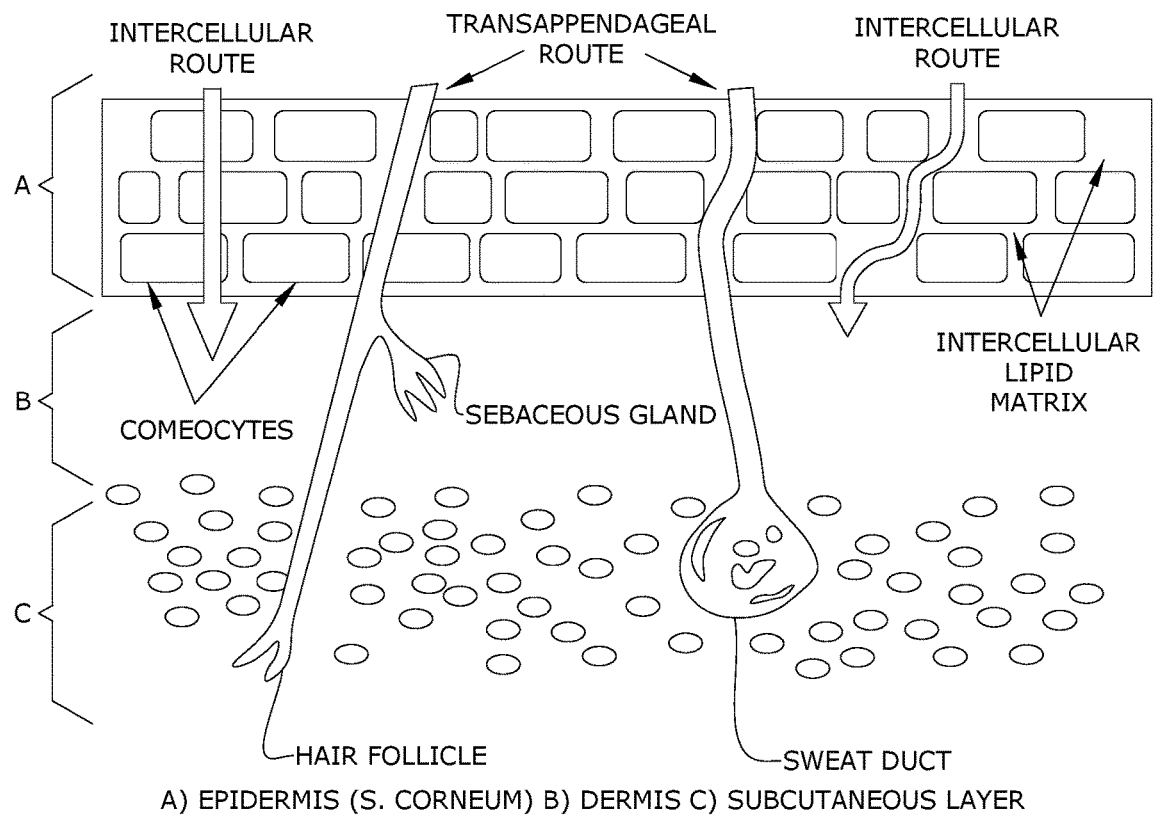
FIG. 7 is an illustration of the epidermis, dermis, and subcutaneous layer.

FIGS. 4 through 7 are schematic views illustrating barriers across which nanoparticles may travel by the inventive method. FIGS. 4 and 5 illustrate nanoparticles interacting with cells.

FIG. 8 shows diffusion of nanobubbles across a membrane over time, illustrating the mechanics of the inventive method. The nanobubbles cross from a region of higher concentration to a region of lower concentration until both regions have equal concentrations.

FIG. 9 is a flow chart of a series of steps of a method according to an embodiment of the present invention. These steps are generally described herein.

It should be understood, of course, that the foregoing relates to exemplary embodiments of the invention and that modifications may be made without departing from the spirit and scope of the invention as set forth in the following claims.

What is claimed is:

1. A therapeutic method of administering nanoparticles, comprising:
    a) providing at least one bootie and a foot bath with a heating element and a vibration element;
    b) adding water at a first temperature to the foot bath;
    c) donning the at least one bootie on a subject's foot;
    d) resting the subject's foot and the at least one bootie in the water in the foot bath for a first predetermined time;
    e) adding a nanoparticle composition to the at least one bootie;
    f) activating the heating element to maintain a second temperature and activating the vibration element after the adding of the nanoparticle composition to the at least one bootie;
    g) resting the subject's foot in the nanoparticle composition in the bootie for a second predetermined time after the first predetermined time;
    h) after the second predetermined time, doffing the at least one bootie, emptying the at least one bootie into the foot bath, and adjusting the foot bath to maintain a third temperature; and
    i) after the emptying the at least one bootie into the foot bath, soaking the subject's foot in the foot bath for a third predetermined time.

2. The therapeutic method of administering nanoparticles of claim 1, further comprising rinsing the subject's foot and drying the subject's foot.

3. The therapeutic method of administering nanoparticles of claim 1, wherein the first temperature is operative to constrict blood vessels in the subject's foot.

4. The therapeutic method of administering nanoparticles of claim 1, wherein the second predetermined time is from about 1 to about 7 times the first predetermined time.

5. The therapeutic method of administering nanoparticles of claim 1, wherein the nanoparticle composition is a nanoparticle solution or a nanoparticle emulsion.

6. The therapeutic method of administering nanoparticles of claim 1, wherein the second temperature is about 80° F. to about 90° F.

7. The therapeutic method of administering nanoparticles of claim 1, wherein the third temperature is operative to dilate blood vessels in the subject's foot.

8. The therapeutic method of administering nanoparticles of claim 1, wherein the third predetermined time is from about 1 to about 2 times the second predetermined time.

9. The therapeutic method of administering nanoparticles of claim 1, wherein the at least one bootie is two booties and two feet are treated.

10. The therapeutic method of administering nanoparticles of claim 1, wherein a sum of the first predetermined time, the second predetermined time, and the third predetermined time is from about 30 minutes to about one hour 15 minutes.

11. The therapeutic method of administering nanoparticles of claim 1, wherein the subject's foot is submersed to above an ankle in the at least one bootie and in the foot bath.

12. A therapeutic nanoparticle diffusion system performing the method of claim 1, the system comprising: at least one rubber bootie adapted to accommodate a user's foot and a nanoparticle composition; a foot bath with a predetermined height and having a vibrational base and a heating element coupled to the foot bath; and the nanoparticle composition.

* * * * *